United States Patent [19]
Boris

[11] Patent Number: 4,588,750
[45] Date of Patent: May 13, 1986

[54] THERAPEUTIC COMPOSITIONS FOR REDUCING SEBUM SECRETION

[75] Inventor: Alfred Boris, Parsippany-Troy Hills, N.J.

[73] Assignee: Hoffmann-La Roche Inc., Nutley, N.J.

[21] Appl. No.: 488,318

[22] Filed: Apr. 25, 1983

Related U.S. Application Data

[63] Continuation-in-part of Ser. No. 394,754, Jul. 2, 1982, abandoned.

[51] Int. Cl.$^4$ ............................................. A61K 31/015
[52] U.S. Cl. ..................... 514/765; 514/852; 514/859; 514/864
[58] Field of Search ........................ 424/356; 585/26; 514/765

[56] References Cited

U.S. PATENT DOCUMENTS 3,822,305 7/1974 Pintschoulos et al. ............ 564/84 X
4,326,055 4/1982 Loeliger .............................. 542/429

OTHER PUBLICATIONS

Rydell et al., Acta Pharmacol. et. Toxicol., 51, 413–420 (1982).
Kistler, Calcif. Tissue Int.; 33, 249–254 (1981).
Loeliger et al., Eur. J. Med. Chem.–Chemica Therapeutica, 15 #1, pp. 9–15 (1980).

Primary Examiner—Leonard Schenkman
Attorney, Agent, or Firm—Jon S. Saxe; George M. Gould; William H. Epstein

[57] ABSTRACT

This invention is directed to methods for and compositions useful in reducing sebum secretion utilizing 1,2,3,4-tetrahydro-1,1,4,4-tetramethyl-6-[α-methylstyryl]naphthalene as an active ingredient.

26 Claims, No Drawings

THERAPEUTIC COMPOSITIONS FOR REDUCING SEBUM SECRETION

CROSS REFERENCE TO RELATED APPLICATION

This application is a continuation-in-part of U.S. patent application Ser. No. 394,754, filed on July 2, 1982 now abandoned.

BACKGROUND OF THE INVENTION AND STATEMENT OF PRIOR ART

Increased sebum secretion is known to be associated with conditions such as oily hair and scalp and Acne Vulgaris, a chronic disorder of the pilosebaceous units primarily involving the face, chest and back. Sebum is produced by the sebaceous glands which normally are found only in association with hair follicles (therefore the terminology pilosebaceous). The gland continuously forms the complex fatty mixture known as sebum which finds passage up the hair follicle.

Disorders such as acne often result when excess sebum is produced, when the pilosebaceous follicular openings are too small to permit the sebum to pass, or when both conditions are present. In addition, acne lesions generally harbor Propionibacterium acnes on culture. P. acnes appears to be the major source of lipolytic anzymes which hydrolyze the triglycerides of sebum to form irritating free fatty acids.

The primary lesion of acne is the comedo. The open comedo (blackhead) consists of a firm mass of keratin and sebum which blocks and dilates the follicular pore. The upper portion of the blackhead is darkened by slow oxidative changes (not by dirt), the lower portions are white. The closed comedo (whitehead) which is a collection of keratin and sebum with the follicular opening blocked, are potentially the starting point of deep inflammatory lesions.

There have been numerous remedies advanced in the art for the symptomatic treatment of disorders related to increased sebum secretion, such as oily scalp, oily hair and acne, by both topical and internal therapy. Cleansing agents such as abrasives, astringents, shampoos, and special soaps, etc., have been used, however these merely remove surface lipids. These agents make the skin, scalp and hair temporarily appear less oily, but have only a temporary effect on the disorder. Topical drying agents such as sulfur, resorcinol, salicylic acid have been used for the treatment of acne in various lotions and creams. Their efficacy lies only in the capacity for producing erythema (reddening) and desquamation (peeling off), and for causing existing comedones, papules and pustules to peel.

Antibiotics have been among the most effective in the treatment of acne. Long term therapy with antibiotics, however, is not satisfactory for a number of reasons, the most prominent of which is the danger of the development of resistant organisms which would then be immune to treatment with the antibiotic in other therapeutic situations. Antibiotic symptomatic therapy of acne has also been characterized by a new flare-up of symptoms and relapses when the medication was discontinued. There is also the danger of sensitizing reactions to antibiotics which may occur with some patients.

The prior art has also utilized stilbene derivatives (see U.S. Pat. No. 4,326,055 issued Apr. 20, 1982 to Loeliger) and retinoic acids, to treat dermatological disorders. Retinoids act by increasing follicular epithelial production of nonadhering cells, thereby dislodging and sloughing off the comedo contents. Retinoids have also been shown to reduce sebaceous gland size and to inhibit sebum secretion. In many cases, however, these retinoids can cause deleterious side effects such as hypervitaminosis.

SUMMARY OF THE INVENTION

In accordance with the present invention, it has been discovered that through the administration of 1,2,3,4-tetrahydro-1,1,4,4-tetramethy-6[α-methylstyryl]naphthalene to patients sebum secretion is reduced. Therefore, the administration of this compound which acts to reduce sebum secretion, provides a means for combatting diseases such as acne, oily hair and oily scalp. In such a manner, the administration of this compound may be used either as a prophylaxis against disorders caused by excess sebum secretion such as acne or oily scalp and hair or in their treatment.

In contrast to the methods of the prior art, the present invention provides new methods and compositions which are both topically and internally effective in reducing sebum secretion, particularly with respect to combatting acne and which, surprisingly, do not have any of the deleterious side effects associated with the prior art. The present invention does not lead to side effects caused by prior art therapeutic modalities such as toxicity, scarring or hypervitaminosis. Furthermore use of this compound does not produce side effects such as toxicity nor does it result in sensitizing reactions or the development of resistant organisms. This compound, in contrast to some other modalities used to treat acne, is not tetratogenic, and is not irritating to the skin when applied topically.

DETAILED DESCRIPTION OF THE INVENTION

The use of the compound 1,2,3,4-tetrahydro-1,1,4,4-tetramethyl-6[α-methylstyryl]naphthalene reduces sebum secretion in persons to whom it is administered. It is known that inhibition of sebum production and/or secretion is effective in the treatment and/or prevention of disorders such as acne. Increased sebum secretion also produces such dermatological conditions such as seborrhea, including dandruff, oily skin, oily hair, whiteheads and blackheads.

Therefore, the method of this invention comprises the topical or internal administration of 1,2,3,4-tetrahydro-1,1,4,4-tetramethyl-6[α-methylstyryl]naphthalene, particularly 1,2,3,4-tetrahydro-1,1,4,4-tetramethyl-6[(E)-α-methylstyryl]naphthalene is preferred, although it is foreseeable that 1,2,3,4-tetrahydro-1,1,4,4-tetramethyl-6[(Z)α-methylstyryl]naphthalene may also be used in the practice of this invention alone or in combination with 1,2,3,4-tetrahydro-1,1,4,4-tetramethyl-6[(E)α-methylstyryl]napthalene. 1,2,3,4-tetrahydro-1,1,4,4-tetramethyl-6[α-methylstyryl]naphthalene is a compound with the structural formula:

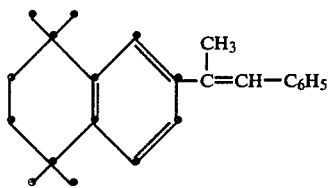

In accordance with this invention the aforementioned naphthalene derivative of formula I can be provided as a means for reducing sebum secretion and thereby is useful as a prophylaxis or means for treating disorders such as acne by administrating it in pharmaceutically acceptable oral, injectable or topical composition and modes. These pharmaceutical compositions of the invention contain said compound of formula I in association with a compatible pharmaceutically acceptable carrier material. Any conventional carrier material can be utilized. The carrier material can be an organic or inorganic inert carrier material suitable for enteral, percutaneous or parenteral administration. Suitable carriers include water, gelatin, gum arabic, lactose, starch, magnesium stearate, talc, vegetable oils, polyalkyleneglycols, petroleum jelly and the like. Furthermore, the pharmaceutical preparations may contain other pharmaceutically active agents. Additional additives such as flavoring agents, preservatives, stabilizers, emulsifying agents, buffers and the like may be added in accordance with accepted practices of pharmaceutical compounding.

The pharmaceutical preparations can be made up in any conventional form including: (a) a solid form for oral administration such as tablets, capsules, pills, powders, granules, and the like; (b) a liquid form for oral administration such as solutions, syrups, suspensions, elixirs and the like; (c) preparations for parenteral administration such as sterile solutions, suspensions or emulsions; and (d) preparations for topical administrations such as solutions, suspensions, ointments, creams, gels, micronized powders, aerosols and the like. The pharmaceutical preparations may be sterilized and/or may contain adjuvants such as preservatives, stabilizers, wetting agents, emulsifiers, salts for varying the osmotic pressure and/or buffers.

For topical administration to the skin the aforementioned derivative is preferably prepared as ointments, tinctures, creams, gels, solutions, lotions, sprays, suspensions, shampoos, hair soaps, perfumes and the like. In fact, any conventional composition utilized for application to the scalp or skin can be utilized in accordance with this invention. Among the preferred methods of applying the composition containing the agents of this invention is in the form of gel, lotion and cream solutions. The pharmaceutical preparation for topical administration to the skin can be prepared by mixing the aforementioned active ingredient with non-toxic, therapeutically inert, solid or liquid carriers customarily used in such preparations. These preparations should contain at least about 0.0005 percent by weight, of the active ingredient based upon the total weight of the composition. Since the active ingredient, the compound of of formula I, is non-toxic, non-tetratogenic and non-irritating it may be used in topical compositions in amounts significantly exceeding 10 percent. However, using the compound of formula I in amounts greater than 10 percent of the total composition yield no substantial therapeutic benefits over that obtained of up to 10 percent. It is therefore preferred that these these preparations contain about 0.01 to 10 percent by weight of the active ingredient based upon the total weight of the composition. It is also preferred to apply these preparations once or twice daily to the skin. These preparations can be applied according to the need of the patient. In carrying out this invention, the active ingredient can be applied in an aqueous solution or an alcohol solution such as ethyl alcohol.

In preparing the topical preparations described above additives such as preservatives, thickeners, perfumes and the like conventional in the art of pharmaceutical compounding of topical preparation can be used. In addition, conventional antioxidants or mixtures of conventional antioxidants can be incorporated into the topical preparations containing the aforementioned active agent. Among the conventional antioxidants which can be utilized in these preparations are included N-methyl-α-tocopherolamine, tocopherols, butylated hydroxyanisole, butylatedhydroxytoluene, ethoxyquin and the like. Cream-base pharmaceutical formulations containing the active agent, used in accordance with this invention, are composed of aqueous emulsions containing a fatty acid alcohol, semi-solid petroleum hydrocarbon, 1,2-ethyleneglycol and an emulsifying agent.

Ointment formulations containing the active agent in accordance with this invention comprises admixtures of a semi-solid petroleum hydrocarbon with a solvent dispersion of the active material. Cream compositions containing the active ingredient for use in this invention preferably comprise emulsions formed from a water phase of a humectant, a viscosity stabilizer and water, an oil phase of fatty acid alcohol, a semisolid petroleum hydrocarbon and an emulsifying agent and a phase containing the active agent dispersed in an aqueous stabilizer-buffer solution. Stabilizers may be added to the topical preparation. Any conventional stabilizer can be utilized in accordance with this invention. In the oil phase, fatty acid alcohol components function as a stabilizer. These fatty acid alcohol components are derived from the reduction of a long-chain saturated fatty acid at least about 14 carbon atoms. Also, conventional perfumes and lotions generally utilized in topical preparation for the hair can be utilized in accordance with this invention. Furthermore, if desired, conventional emulsifying agents can be utilized in the topical preparations of this invention.

Parenteral dosage forms may be infusions or injectable solutions which can be injected intravenously or intramuscularly. These preparations can also contain other medicinally active substances. For parenteral formulations a daily dosage of from about 0.01 mg to about 2 mg per Kg of body weight, preferably from about 0.025 mg to about 0.5 mg per kg of body weight of the patient will be utilized. Additional additives such as flavoring agents, preservatives, stabilizers, emulsifying agents, buffers and the like may be added in accordance with accepted practices of pharmaceutical compounding.

A preferred oral dosage form comprises capsules of hard or soft gelatin methylcellulose or of another suitable material easily dissolved in the digestive tract. The enteral dosages contemplated in accordance with the present invention will vary in accordance with the needs of the individual patient as determined by the prescribing physician. Generally, however, a daily dosage of from about 0.01 mg. to about 2 mg per Kg of body weight and preferably from about 0.025 mg. to about 0.5 mg per kg of body weight of the patient is utilized. This dosage may be administered according to any dosage schedule determined by the physician in accordance with the requirements of the patient.

It is likewise within the purview of the present invention to incorporate the therapeutically active substance enumerated herein in any desired amount for enteral administration within the oral unit dosage form. It is preferred, however, to formulate preparations containing the active substance of the present invention in such a manner that each dose contains from about 0.05 mg to about 100 mg, particularly from about 0.1 mg to about 10 mg of the active substance with suitable therapeutically inert fillers and diluents. It is especially preferred to incorporate such a dosage into soft gelatin capsules and tablets.

In accordance with this invention, therefore, 1,2,3,4-tetrahydro-1,1,4,4-tetramethyl-6-[α-methylstyryl]naphthalene, which shows a pronounced sebum suppressing activity, can thus be used in the pharmaceutical preparations mentioned above, for reducing sebum secretion and for the treatment of acne.

The dosage for treatment typically depends on the route of administration, the age, weight and acne condition of the individual. The following examples illustrate pharmaceutical preparations containing the naphthalene derivative provided by the present invention. In the following examples the compound 1,2,3,4-tetrahydro-1,1,4,4-tetramethyl-6-[(E)α-methylstyryl]naphthalene is designated by the symbol (I) under the column entitled "ingredient".

EXAMPLE 1

| Tablets containing the following ingredients are prepared: | | | | |
|---|---|---|---|---|
| Item | Ingredient | mg./tablet | mg./tablet | mg./tablet |
| 1. | (I) | 1.0 | 5.0 | 10.0 |
| 2. | Lactose, Anhydrous | 127.0 | 142.5 | 182.0 |
| 3. | Microcrystalline Cellulose | 40.0 | 50.0 | 60.0 |
| 4. | Modified Starch | 10.0 | 12.5 | 15.0 |
| 5. | Cornstarch | 20.0 | 25.0 | 30.0 |
| 6. | Magnesium Stearate | 2.0 | 2.5 | 3.0 |
| | Total | 200 mg | 237.5 mg | 300 mg |

The ingredient items 1,2,3,4 and 5 are mixed from about 1 to about 15 minutes. Item 6 is then added and the resultant mixture is mixed for about an additional 5 minutes. The resulting mixture is compressed into tablet form.

EXAMPLE 2

| Capsules containing the following ingredients are prepared: | | |
|---|---|---|
| Item | Ingredient | mg/capsule |
| 1. | (I) | 100 |
| 2. | Lactose | 99 |
| 3. | Corn starch | 20 |
| 4. | Talc | 5 |
| 5. | Magnesium stearate | 1 |
| | Fill weight of capsule | 225 mg |

The ingredient items 1,2 and 3 are mixed and then milled. The resulting mixture is then mixed with ingredient items 4 and 5 and is then filled into capsules of appropriate size.

EXAMPLE 3

| Tablets containing the following ingredients are prepared: | | | | |
|---|---|---|---|---|
| Item | Ingredient | mg/tablet | mg/tablet | mg/tablet |
| 1. | (I) | 1.0 | 5.0 | 10.0 |
| 2. | Lactose | 195.0 | 230.0 | 264.0 |
| 3. | Pregelatinized Starch | 12.5 | 15.0 | 17.5 |
| 4. | Cornstarch | 25.0 | 30.0 | 35.0 |
| 5. | Modified Starch | 12.5 | 15.0 | 17.5 |
| 6. | Magenesium Stearate | 4.0 | 5.0 | 6.0 |
| | Total | 250 mg | 300 mg | 350 mg |

The ingredient items 1,2,3,4 and 5 are mixed, granulated with water and then dried. The dried mixture is then milled. Ingredient item 6 is then added to the milled mixture and the resultant mixture is then compressed into tablet form.

This compound of formula I is effective for use with acne in various mammals as can be seen from the following test.

The effect of the (E) form of the compound of formula I on sebum secretion in mammals, such as rats, was determined according to the following procedure. Male rats weighing about 50–60 g. were castrated at the age of 21–22 days. One week after surgery, the rats were washed in a detergent solution to remove "sebum" which was secreted prior to the test period. One group of rats were treated only with the carrier vehicles employed. Another group of rats received only testosterone propionate in sesame oil, 100 ug/0.2 ml/rat/day simultaneously. Other groups of rats were given testosterone propionate in sesame oil (100 ug/0.2 ml/rat/day subcutaneously) and 1,2,3,4-tetrahydro-1,1,4,4-tetramethyl-6-[(E)-α-methylstyryl]naphthalene, with different amounts of 1,2,3,4-tetrahydro-1,1,4,4-tetramethyl-6[(E)-α-methylstyryl]naphthalene being administered to each of the other groups orally in 0.2 ml/rat/day propylene glycol. The rats were treated with the compounds for 14 days. On the 15th day total body immersion in a fixed volume of acetone with mixing for two minutes removed surface "sebum" from skin and fur. An aliquot of the solvent bath was dried and the solid residue was measured gravimetrically. Inhibition of the testosterone-stimulated increase in "sebum" over solely testosterone propionate stimulated rats was used as the parameter of response. The results are shown in Table I.

TABLE I

| T.P. ug/rat/ day, s.c. | 1,2,3,4-tetrahydro-1,1,4,4-tetramethyl-6-[(E)-α-methylstyryl] naphthalene ug/rat/day, p.o. | No. of Rats | Mean ± S.E. "Sebum" (ug/100 ul) |
|---|---|---|---|
| 0 | 0 | 8 | 15.5 ± 1.4*** |
| 100 | 0 | 8 | 25.1 ± 1.4 |
| 100 | 0.5 | 8 | 25.1 ± 1.9 NS |
| 100 | 1 | 8 | 26.8 ± 1.6 NS |
| 100 | 2 | 8 | 22.1 ± 1.2 NS |
| 100 | 4 | 8 | 21.6 ± 1.6 NS |
| 0 | 0 | 9 | 19.1 ± 0.7*** |
| 100 | 0 | 9 | 30.1 ± 1.0 |
| 100 | 10 | 9 | 23.4 ± 1.6**(61% I) |
| 100 | 20 | 9 | 22.4 ± 1.6**(70% I) |
| 100 | 40 | 9 | 22.1 ± 0.9***(73% I) |
| 100 | 100 | 9 | 19.9 ± 1.2***(93% I) | p<.01,*p<.001, NS = not significant when compared to group receiving T.P. (testosterone propionate) alone.
% I = % Inhibition of testosterone-stimulated increase in "sebum".

As can be seen from these results, sebum secretion decreased to virtually normal level in rats given 100 ug/rat/day, p.o. of 1,2,3,4-tetrahydro-1,1,4,4-tetramethyl-6-[(E)-α-methylstyryl]naphthalene and 100 ug/rat/day, subcutaneously of testosterone propionate as compared to that level of sebum secretion reached in rats whose sebum secretion had been stimulated and increased to above normal levels with 100 ug/rat/day, subcutaneously testosterone propionate alone.

The effect of the (E) form of the compound of formula I on sebaceous glands in mammals was further determined using hamsters, according to the following procedure. Male hamsters were castrated at eight weeks of age and one week after surgery were treated with 4 ug testosterone propionate and 1,2,3,4-tetrahydro-1,1,4,4,-tetramethyl-6-[(E)-α-methylstyryl]naphthalene topically in acetone on the flank organs. Animals were treated for 14 days and the response was measured by weight changes in flank organs removed at autopsy. Separate groups of hamsters served as vehicle controls and testosterone alone groups. Activity was measured by inhibition of the increase in weight which occurs in response to stimulation with testosterone propionate. The results are shown in Table II.

TABLE II

| Treatment | Hamsters | |
|---|---|---|
| | No. of Hamsters | Mean ± S.E. Flank Organ (mg) |
| Acetone, 50 ul | 7 | 13.2 ± 0.7*** |
| T.P., 5 ug | 8 | 33.8 ± 2.0 |
| T.P., 5 ug & 1,2,3,4-tetrahydro-1,1,4,4-tetramethyl-6-[(E)-α-methylstyryl]napthalene, 0.5 μg | 9 | 26.0 ± 1.6***(38% I) |

***p <.001, NS = not significant when compared to group receiving T.P. (testosterone propionate) alone.
% I = % Inhibition of testosterone-stimulated increase in flank organ weight.

As can be seen from these results when 1,2,3,4-tetrahydro-1,1,4,4-tetramethyl-6-[(E)-α-methylstyryl]naphthalene was provided at a dosage of 0.5 ug/animal/day topically together with 5 μg T.P. there resulted approximately a 38 percent inhibition of flank organ weight increase when compared to the flank organ weight of hamsters which were treated with testosterone alone.

The effect of the (E) form of the compound of formula I on sebaceous glands in mammals was further determined using gerbils, according to the following procedure. Male gerbils were castrated at 8 weeks of age and one week after surgery were treated with 5 ug free testosterone and 1,2,3,4-tetrahydro-1,1,4,4-tetramethyl-6-[(E)-α-methylstyryl]naphthalene topically in acetone on the abdominal sebaceous gland pad organs. Animals were treated for 14 days and the response was measured by weight changes in these organs removed at autopsy. Separate groups of gerbils served as vehicle controls and testosterone alone groups. Activity was measured by inhibition of the increase in weight which occurs in response to stimulation with testosterone. The results are shown in Table III.

TABLE III

| Treatment | Gerbils | |
|---|---|---|
| | No. of Gerbils | Mean ± S.E. Sebaceous Gland Pad mg |
| Acetone, 50 ul | 9 | 22.4 ± 3.3*** |
| Testosterone, 5 ug | 10 | 72.5 ± 5.8 |
| Testosterone, 5 ug & 1,2,3,4-tetrahydro 1,1,4,4-tetramethyl-6-[(E)-α methylstyryl]napthalene, 1 ug | 10 | 45.6 ± 6.9**(54% I) | p <.01, *p <.001, NS = not significant when compared to group receiving testosterone alone.
% I = % Inhibition of testosterone-stimulated increase in sebaceous gland pad weight.

As can be seen these results when 1,2,3,4-tetrahydro-1,1,4,4-tetramethyl-6-[(E)-α-methylstyryl]naphthalene was provided at a dosage of 1.0 ug/animal/day p.o. with 5 ug testosterone topically there resulted approximately a 54 percent inhibition of sebaceous gland pad weight over the level of sebum secretion when gerbils were treated topically with 5 ug testosterone alone.

The 1,2,3,4-tetrahydro-1,1,4,4-tetramethyl-6-[(E)-α-methylstyryl]naphthalene shows no undesired side effects such as hypervitaminosis at pharmaceutically suitable dosages. This is also noted by the prior art, see Loeliger et al., "Arotinoids, a new class of highly active retinoids, "*Eur. J. Med. Chem.*, 15, 9(1980) which shows this compound to have no effect on papilloma growth. Indeed this article shows that after intraperitoneal administration of this compound, there was an increase in papilloma size in the test animal. The lack of undesired side effects is illustrated by the following procedure.

A hypervitaminosis A test was carried out on mice weighing 25-27 g. which received i.p. injections of 1,2,3,4-tetrahydro-1,1,4,4-tetramethyl-6-[(E)-α-methylstyryl]naphthalene in arachis oil over a 14 day period. Hypervitaminosis A is defined as being that condition of the animals where the symptoms (weight loss, skin desquamtion, loss of hair, bone fractures of extremities) added up to at least 3, c.f. W. Bollag, Cancer, 1974, 10, 731. In this test 1,2,3,4-tetrahydro-1,1,4,4-tetramethyl-6-[(E)-α-methylstyryl]naphthalene does not result in hypervitaminosis A even at a dosage of up to 400 mg/kg.

In order to further determine the safety of the (E) form of the compound of formula I teratogenicity tests, for fetal abnormalities, were carried out in rats according to the following procedure. 1,2,3,4-tetrahydro-1,1,4,4-tetramethyl-6-[(E)-α-methylstyryl]naphthalene was provided to Charles River CD rats on gestation days 8 and 9 using a daily dose of 10, 50 or 150 mg/kg of this substance dissolved or suspended in a polyethelene glycol formulation containing traces of antioxidants (ascorbyl palmitate and butylated hydroxyanisole). The compound was administered orally at a constant volume of 5 ml/kg. The rats were then sacrificed on gestation day 20 and examined. In all of these tests, there were no adverse effects on the maternal body weights, the absorption rate or fetal weight; also no external malformations were recorded in any of the 187 fetuses thereby further demonstrating the safety of this compound.

The lack of skin irritation of the (E) form of the compound of formula I, when used in a topical preparation, was demonstrated by the following procedure. 1,2,3,4-tetrahydro-1,1,4,4-tetramethyl-6-[(E)-α-methylstyryl]naphthalene was applied topically to the ears of 21-day-old male Charles River CD-1 mice for 7 consecutive days in 25 μl/day acetone. During treatment mice are observed for development of erythema on the ears, and uniform skin punches are taken at autopsy on day 8. Wet and dry weights of the skin samples were determined and compared to weights from vehicle-treated control animals. Increases in fluid content of the skin punches served as a measure of edema when irritation and inflammation had occurred. 1,2,3,4-tetrahydro-1,1,4,4-tetramethyl-6-[(E)-α-methylstyryl]naphthalene was shown not to have adverse effects when applied topically at doses up to 100 μg/day thereby demonstrating the lack of skin irritation of the (E) form of the compound of formula I when used in a topical preparation.

It is readily apparent from the above that 1,2,3,4-tetrahydro-1,1,4,4-tetramethyl-6-[(E)-α-methylstyryl]-naphthalene is well tolerated without toxic symptoms in the pharmacologically suitable dosages and further support the efficacy of the aforementioned naphthalene derivative in the treatment of acne.

In addition, although 1,2,3,4-tetrahydro-1,1,4,4-tetramethyl-6-[(E)-α-methylstyryl]naphthalene is a known compound, its preparation is described below for the sake of completeness.

10 G. of benzaldehyde (freshly distilled) were added to 60 g. of triphenyl-[1-(5,6,7,8-tetrahydro-5,5,8,8-tetramethyl-2-naphthyl)ethyl]phosphonium bromide. The mixture was refluxed under argon for 30 hours. The so-obtained clear, yellow solution was cooled and poured into 600 ml. of methanol/water (6:4 parts by volume). The mixture was extracted four times with hexane, the organic phase washed once with methanol/water (6:4 parts by volume) and three times with water, dried with sodium sulfate and evaporated. The oily residue was filtered through a short silica gel column with hexane containing 5% ethyl acetate and was recrystallized from hexane yielding 1,2,3,4-tetrahydro-1,1,4,4-tetramethyl-6-[(E)-α-methylstyryl]naphthalene as colorless crystals, m.p. 83°-85° C.

I claim:

1. A method for reducing sebum secretion which comprises the administration to patients of a composition containing a present in an amount effective for reducing sebum secretion, said compound being represented by the following structural formula:

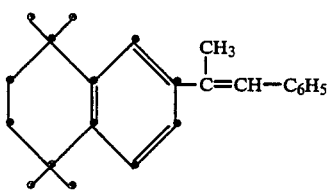

2. The method of claim 1 wherein the compound is 1,2,3,4-tetrahydro-1,1,4,4-tetramethyl-6[(E)α-methylstyryl]naphthalene.

3. A method in accordance with claim 2 wherein said composition is administered orally.

4. A method in accordance with claim 3 wherein said composition is administered in the form of an oral pharmaceutical unit dosage form, each unit dosage form containing from about 0.05 mg to about 100 mg of 1,2,3,4-tetrahydro-1,1,4,4-tetramethyl-6-[(E)α-methylstyryl]naphthalene.

5. A method in accordance with claim 1 wherein said composition is administered topically.

6. A method in accordance with claim 5 wherein said composition is administered in topical preparation said preparation containing at least 0.0005 percent by weight of 1,2,3,4-tetrahydro-1,1,4,4-tetramethyl-6-[(E)α-methylstyryl]naphthalene.

7. A method for combatting seborrhea which comprises the administration to patients an effective amount of a composition comprising a therapeutically inert pharmaceutically acceptable carrier and a compound represented by the following structural formula:

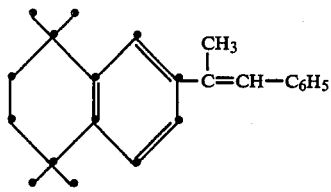

8. The method of claim 7 wherein said compound is 1,2,3,4-tetrahydro-1,1,4,4-tetramethyl-6[(E)-α-methylstyryl]naphthalene.

9. A method in accordance with claim 8 wherein said composition is administered orally.

10. A method in accordance with claim 8 wherein said composition is administered parenterally.

11. A method in accordance with claim 8 wherein said composition is administered topically.

12. A method for the treatment of dandruff which comprises the administration to patients of an effective amount of a composition comprising a therapeutically inert pharmaceutically acceptable carrier and a compound represented by the following structural formula:

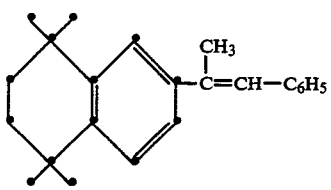

13. The method of claim 12 wherein said compound is 1,2,3,4-tetrahydro-1,1,4,4-tetramethyl-6[(E)-α-methylstyryl]naphthalene.

14. The method of claim 13 wherein said composition further comprises a hair soap.

15. A method for combatting acne comprising administering to a patient a composition containing a pharmaceutically acceptable inert carrier and as an active ingredient the compound 1,2,3,4-tetrahydro-1,1,4,4-tetramethyl-6[α-methylstyryl]naphthalene, said composition being administered in an amount effective to combat acne.

16. The method of claim 15 wherein said compound is 1,2,3,4-tetrahydro-1,1,4,4-tetramethyl-6-[(E)-α-methylstyryl]naphalene.

17. A method in accordance with claim 16 wherein said composition is administered orally.

18. A method in accordance with claim 16 wherein said composition is administered topically.

19. A method in accordance with claim 16 wherein said composition is administered as a prophylaxis against acne.

20. A method in accordance with claim 16 wherein said composition is administered as a treatment for acne.

21. A composition in an oral unit dosage form comprising from about 0.05 to about 100 mg of 1,2,3,4-tetrahydro-1,1,4,4-tetramethyl6-[α-methylstyryl]naphthalene and a therapeutically inert pharmaceutically acceptable carrier.

22. The composition of claim 21 wherein said napthalene compound is 1,2,3,4-tetrahydro-1,1,4,4-tetramethyl-6[(E)-α-methylstyryl]naphthalene.

23. The composition of claim 22 wherein said oral unit dosage form is a tablet or capsule.

24. A composition for topical administration comprising a therapeutically inert pharmaceutically acceptable carrier and from about 0.0005 percent to about 10 percent of 1,2,3,4-tetrahydro-1,1,4,4-tetramethyl-6-[α-methylstyryl]naphthalene.

25. The composition of claim 24 wherein said napthalene compound is 1,2,3,4-tetrahydro-1,1,4,4-tetramethyl-6[(E)-α-methylstyryl]naphthalene.

26. The composition of claim 25 wherein said topical composition is in the form of a lotion, soap, shampoo, cream, gel, ointment or spray.

* * * * *